(12) United States Patent
Ailinger et al.

(10) Patent No.: US 6,733,440 B2
(45) Date of Patent: May 11, 2004

(54) APPARATUS AND METHOD FOR FORMING THIN-WALLED ELASTIC COMPONENTS FROM AN ELASTOMERIC MATERIAL

(75) Inventors: Robert Ailinger, Norwood, MA (US); Stephen Martone, Westford, MA (US)

(73) Assignee: Vision Sciences, Inc., Natick, MA (US)

( * ) Notice: Subject to any disclaimer, the term of this patent is extended or adjusted under 35 U.S.C. 154(b) by 0 days.

(21) Appl. No.: 09/930,712

(22) Filed: Aug. 14, 2001

(65) Prior Publication Data

US 2002/0013511 A1 Jan. 31, 2002

Related U.S. Application Data

(62) Division of application No. 09/235,355, filed on Jan. 21, 1999, now Pat. No. 6,350,231.

(51) Int. Cl.[7] .................................................. A61B 1/00
(52) U.S. Cl. ....................................... 600/121; 600/920
(58) Field of Search ................................. 600/121, 124, 600/125, 920; 264/291, 319, 292

(56) References Cited

U.S. PATENT DOCUMENTS

| | | | |
|---|---|---|---|
| 3,794,091 A | 2/1974 | Ersek et al. ............... 150/52 R |
| 3,805,770 A | 4/1974 | Okada ............................ 128/4 |
| 3,809,072 A | 5/1974 | Ersek et al. .................... 128/23 |
| 4,143,423 A | 3/1979 | Sternlieb ........................ 2/168 |
| 4,459,255 A | * | 7/1984 | Sheridan ...................... 264/102 |
| 4,551,292 A | * | 11/1985 | Fletcher et al. .............. 264/139 |
| 4,794,920 A | 1/1989 | Robichaud ................... 128/844 |
| 4,881,553 A | 11/1989 | Grossman ................... 128/844 |
| 4,886,049 A | 12/1989 | Darras ............................ 128/4 |
| 4,971,071 A | 11/1990 | Johnson ....................... 128/842 |
| 5,098,755 A | 3/1992 | Tanquary et al. ........... 428/35.5 |
| 5,111,831 A | 5/1992 | Foggia ........................ 128/842 |
| 5,237,984 A | 8/1993 | Williams, III et al. .......... 128/4 |
| 5,337,734 A | * | 8/1994 | Saab ........................... 600/121 |
| 5,386,817 A | * | 2/1995 | Jones ........................... 600/104 |
| 5,419,310 A | 5/1995 | Frassica et al. ................. 128/4 |
| 5,429,118 A | 7/1995 | Cole et al. ................... 600/121 |
| 5,443,781 A | * | 8/1995 | Saab ........................... 264/291 |
| 5,482,053 A | 1/1996 | Kelly .......................... 128/844 |
| 5,483,951 A | * | 1/1996 | Frassica et al. ............. 600/104 |
| 5,505,686 A | 4/1996 | Willis et al. ................. 600/104 |
| 5,513,654 A | 5/1996 | Delson ........................ 128/844 |
| 5,570,692 A | 11/1996 | Morinaga ............... 128/662.05 |
| 5,643,175 A | 7/1997 | Adair .......................... 600/133 |
| 5,695,454 A | 12/1997 | Mourkidou .................. 600/166 |
| 5,718,861 A | 2/1998 | Andrews et al. ............. 264/235 |
| 5,881,386 A | * | 3/1999 | Horwege et al. ............. 2/161.7 |
| 6,016,570 A | * | 1/2000 | Vande Pol et al. ........... 2/161.7 |
| 6,270,484 B1 | 8/2001 | Yoon ........................... 604/264 |
| 6,293,907 B1 | * | 9/2001 | Axon et al. .................. 600/114 |
| 6,306,514 B1 | * | 10/2001 | Weikel et al. ............... 428/451 |
| 6,350,231 B1 | * | 2/2002 | Ailinger et al. ............. 600/121 |

* cited by examiner

*Primary Examiner*—Beverly M. Flanagan
(74) *Attorney, Agent, or Firm*—Dorsey & Whitney, LLP

(57) ABSTRACT

A thin-walled elastic sheath that can be stretched axially over an elongated imaging device to closely conform to the device and isolate the device from an external environment, and a method of forming such a sheath, are shown and described. The method includes the steps of heating at least a portion of a sheet of an elastomeric material to an elevated temperature to form a malleable heated portion of the sheet, pressing an elongated forming tool against the sheet at a location central with respect to the heated portion of the sheet, stretching the heated portion of the elastomeric material with the forming tool until an elastic conforming portion of the sheet is conformed to at least a portion of the length of the forming tool, and removing the forming tool from the conforming portion of the sheet to leave the thin-walled, elastic sheath having a wall thickness approximately equal to or less than 0.006 inches.

47 Claims, 8 Drawing Sheets

APPARATUS AND METHOD FOR FORMING THIN-WALLED ELASTIC COMPONENTS FROM AN ELASTOMERIC MATERIAL

CROSS-REFERENCE TO RELATED APPLICATIONS

This application is a divisional of U.S. patent application Ser. No. 09/235,355, filed Jan. 21, 1999 now U.S. Pat. No. 6,350,231.

TECHNICAL FIELD

The present invention is directed toward elongated imaging components and a method of making the components, and, more particularly, toward thin-walled, elastic sheaths for elongated imaging equipment and a method of making the same.

BACKGROUND OF THE INVENTION

The use of intrabody medical equipment, such as endoscopes, catheters, and the like, for diagnostic and therapeutic indications is rapidly expanding. To improve performance, the equipment has been optimized to best accomplish the selected purpose. As an example, endoscopes have been optimized and refined so as to provide upper endoscopes for the examination of the esophagus, stomach, and duodenum, colonoscopes for examining the colon, angioscopes for examining blood vessels, bronchoscopes for examining bronchi, laparoscopes for examining the peritoneal cavity, arthroscopes for examining joints and joint spaces, nasopharygoscopes for examining the nasal passage and pharynx, and intubation scopes for examination of a person's airway.

Optimization of intrabody medical equipment for such therapeutic and diagnostic procedures has resulted in sterile, inexpensive disposable components that are used alone or with non-disposable equipment. In the field of endoscopes, a conventional endoscope 10, shown in FIG. 1, has an insertion tube 12 connected at its proximal end 14 to a handle or control body 16. The insertion tube 12 is adapted to be inserted into a patient's body cavity to perform a selected therapeutic or diagnostic procedure. The insertion tube 12 contains an imaging system 18 having optical fibers or the like extending along the length of the insertion tube and terminating at a viewing window 19 in the insertion tube's distal end 20. The imaging system 18 conveys an image from the viewing window 19 to an eyepiece 22 on the control body 16 or to a monitor (not shown), so the user can see into a selected body cavity during an endoscopic procedure. The endoscope 10 is described in greater detail in U.S. Pat. No. Re 34,110 and U.S. Pat. No. 4,646,722, which are incorporated herein by reference.

Disposable endoscopic sheath assemblies are used to cover the insertion tube 12 and protect it from contaminating a patient during use. Accordingly, the sheath assemblies alleviate the problem and cost of cleaning and sterilizing the insertion tube 12 between endoscopic procedures. The sheaths and endoscopes are usable in medical applications and also in industrial applications, such as visually inspecting difficult to reach areas in an environment that could damage or contaminate the endoscope. As an example, a sheathed endoscope can be used in an industrial area wherein the sheath protects the endoscope's insertion tube from adhesive or the like. As seen in FIG. 1, a conventional sheath assembly 24, shown partially cut away for illustrative purposes, includes a sheath 26 that surrounds the endoscope's insertion tube 12. The sheath assembly 24 may also contain one or more working channels 32 that extend along the insertion tube 12 and that are adapted to receive conventional endoscopic accessories therethrough without allowing the endoscope to contaminate the accessories during the endoscopic procedure. The sheath 26 has a distal end portion 21 that includes an endcap 34 having a transparent window 28 positioned to cover the viewing window 19 at the insertion tube's distal end 20 when the sheath assembly 24 is installed. The endcap 34 is sealably secured to the sheath's distal end portion 21.

The sheath 26 and endcap 34 are commonly made from polymeric materials. The sheath 26 can be made from an inelastic polymer, such as PVC, acrylic, polycarbonate, polyethylene terephthalate or other thermoplastic polyesters, or can be made from an elastomeric material. Both materials presently have advantages and disadvantages.

Inelastic materials allow for thin-walled medical components that exhibit high strength and visible clarity. Using inelastic materials, the sheath 26 can be formed with a thin wall (measuring 0.003 inches or less) and a small diameter (such as 0.5 mm). Inelastic materials tend to be clearer than the elastic materials, and can thus provide better visibility with less distortion.

U.S. Pat. No. 5,443,781 to Saab teaches a method of forming an inelastic, disposable sheath with an integral, optically transparent window. Saab teaches forming the inelastic sheath by heating a sheet or film of optically transparent, inelastic, polymeric material until the material is malleable. As shown in FIG. 2, a mandrel 35 is thrust into the heated film 37 causing the film to stretch and to generally conform to the mandrel's shape. As a result, the heated film 37 is formed into an inelastic closed-end sheath 39 having sidewalls 36, a flange or collar 38 at its open proximal end 40, and a closed distal end 42.

U.S. patent application Ser. No. 08/948,615, which is incorporated herein by reference, further teaches a method of forming an inelastic, endoscopic sheath for use on an insertion tube having a complex cross-sectional shape. The process applies a differential pressure to the outside and inside of the sheath during fabrication to conform the sheath to the shape of a mandrel. By selecting a mandrel with the proper complex shape, the end cap can closely receive the corresponding insertion tube.

Inelastic materials, however, have a number of disadvantages. Tight-fitting sheaths formed from inelastic materials may overly restrict bending when used with flexible insertion tubes. The insertion tube combined with the tight-fitting, inelastic sheath can only bend over a limited radius. If bent further, the sheath will either buckle, in the case of a thick-walled sheath, or the sheath material will become taught, in the case of a thin-walled sheath, preventing the insertion tube from bending further. Consequently, if the inelastic sheath is to be used in combination with a flexible endoscope, the sheath is typically either baggy or must contain bending features, such as accordion-like baffles or the like, as taught by Saab, to allow the insertion tube to sufficiently bend. Both baggy sheaths and these additional bending features add to the cross-sectional size of the sheath during use, which may result in additional pain or discomfort to the patient.

The sheath made from inelastic material cannot be stretched axially onto the insertion tube. As a result, the inelastic sheath does not provide axial tension in the sheath urging the transparent window of the sheath against and in alignment with the viewing window at the insertion tube's distal end. To retain the transparent window in position, additional features, such as connectors or helical coils, are typically built into the sheath. These features add to the complexity and cost of the sheath.

Conventional elastic sheaths have been developed and used with imaging devices such as endoscopes to overcome the drawbacks associated with the inelastic sheaths described above and to provide additional benefits. As an example, conventional elastic sheaths are designed so the sheath will easily bend with the insertion tube without substantially affecting the insertion tube's bending characteristics. The elastic sheath can also be stretched axially over the insertion tube to provide axial tension that retains the transparent window on the sheath against and in alignment with the viewing window at the insertion tube's distal end. The elastic sheath can be designed to closely or tightly cover the insertion tube while still being able to bend with the insertion tube, so the elastic sheath does not need additional bending features.

Elastic materials, however, also have some disadvantages. First, conventional elastic sheaths are manufactured by extruding elastomeric material, that is, by pushing or forcing the elastomeric material through a die to form the desired structure. The extruded elastic sheaths, however, have manufacturing limits that restrict the minimum wall thickness of the sheath. Efforts toward manufacturing such a sheath have typically resulted in the extruded material collapsing or wrinkling during the process. As a result, the extruded elastic sheath must be made with a relatively thick wall (i.e., greater than 0.006 inches). The thicker the sheath wall in a tight-fitting sheath, the greater the resistance to bending.

Tight fitting, elastic sheaths can also be complex and expensive to install onto the insertion tube. The elastic materials commonly used to manufacture the sheath have high friction characteristics. As a result, it can be difficult to insert the insertion tube into the tight-fitting sheath because the insertion tube binds on the inner wall of the sheath. One solution is to make the sheath with a diameter considerably larger than the insertion tube, so the sheath is baggy when installed on the insertion tube. Baggy sheaths, however, are undesirable in many endoscopic procedures because the sheath can be twisted, bunched, or misaligned relative to the insertion tube during the procedure. The baggy sheath can also increase the diameter of the sheathed insertion tube, which can increase pain or discomfort to the patient. In another solution, a tight-fitting sheath and endoscope are specially designed to mate with a vacuum or inflation chamber (not shown) that radially expands the sheath while the insertion tube is inserted into the sheath. Once the insertion tube is fully inserted into the sheath, the vacuum or inflation pressure is removed and the sheath contracts to a size that fits closely over the insertion tube. The equipment needed for this installation process, however, as well as the time required to learn and perform the process, can significantly increase the cost of endoscopic procedures.

In the design of intrabody medical devices and accessories, including optical and non-optical devices, there is a need for components having the benefits of both elastic and inelastic materials while, at the same time, avoiding the disadvantages associated with these materials. As an example, there is a need for an elastic component that can be manufactured with both a thin wall and a small internal diameter. There is also a need for a small diameter, elastic sheath that can be quickly and inexpensively installed and used on a flexible insertion tube. Other medical devices and accessories would also benefit by such inexpensive, elastic, thin-walled components.

SUMMARY OF THE INVENTION

The present invention provides a method capable of forming thin-walled, elastic medical components from a heated, elastomeric sheet. The method of one particular embodiment of the invention may be used to manufacture small-diameter, thin-walled, elastic components, which has been problematic in the prior art. In an exemplary embodiment of the present invention, the method of forming a small-diameter, thin-walled elastic component includes heating a portion of the elastomeric sheet to a malleable temperature, pressing a distal end of an elongated forming tool on a first side of the elastomeric sheet at a location in the heated portion, stretching the heated portion with the forming tool until an elastic conforming portion is closely conformed to a portion of the forming tool, and removing the forming tool from the conforming portion of the sheet. The method of this embodiment can be used to form an elastic sheath having a thin wall, a small diameter, and a length shorter than the length of the insertion tube so that the elastic sheath may be stretched longitudinally over the insertion tube.

Embodiments of the present invention also provide a non-extruded thin-walled, elastic medical component made by the above-described process.

DETAILED DESCRIPTION OF THE INVENTION

The present detailed description is generally directed toward elastomeric sheaths for medical devices, and toward a method for forming such sheaths from a sheet of an elastomeric material. Many specific details of certain embodiments of the invention are set forth in the following description and in FIGS. 3–10 to provide a thorough understanding of such embodiments. One skilled in the art, however, will understand that the present invention may have additional embodiments, or that the invention may be practiced without several of the details described in the following description.

Figure 1:
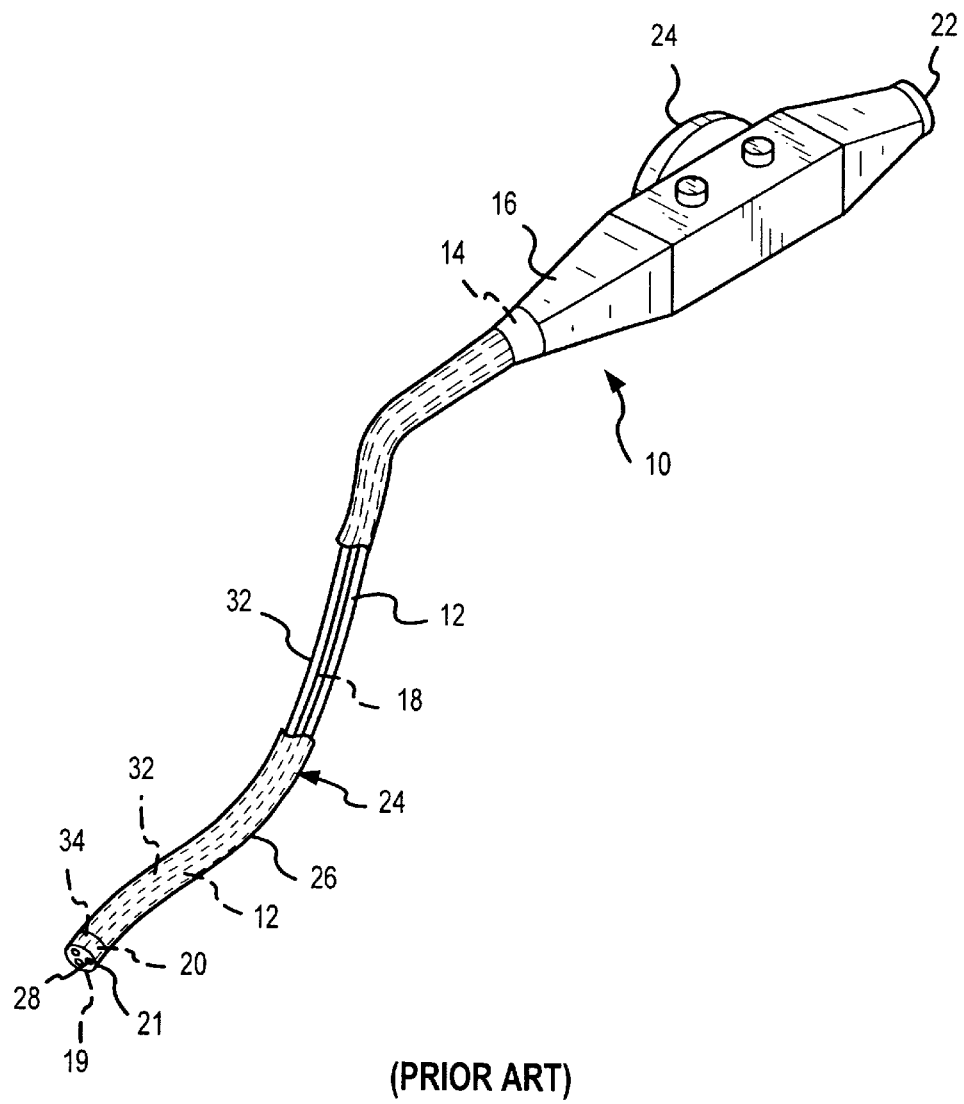
FIG. 1 is an isometric view of a prior art endoscope and endoscopic sheath assembly.
Figure 2:
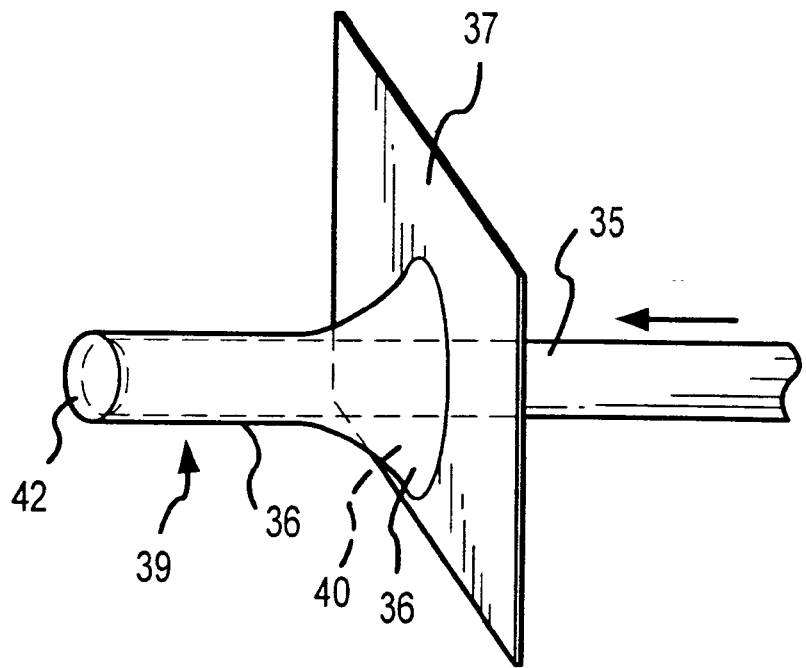
FIG. 2 is an isometric view of an inelastic film of the prior art being stretched by a mandrel.
Figure 3:
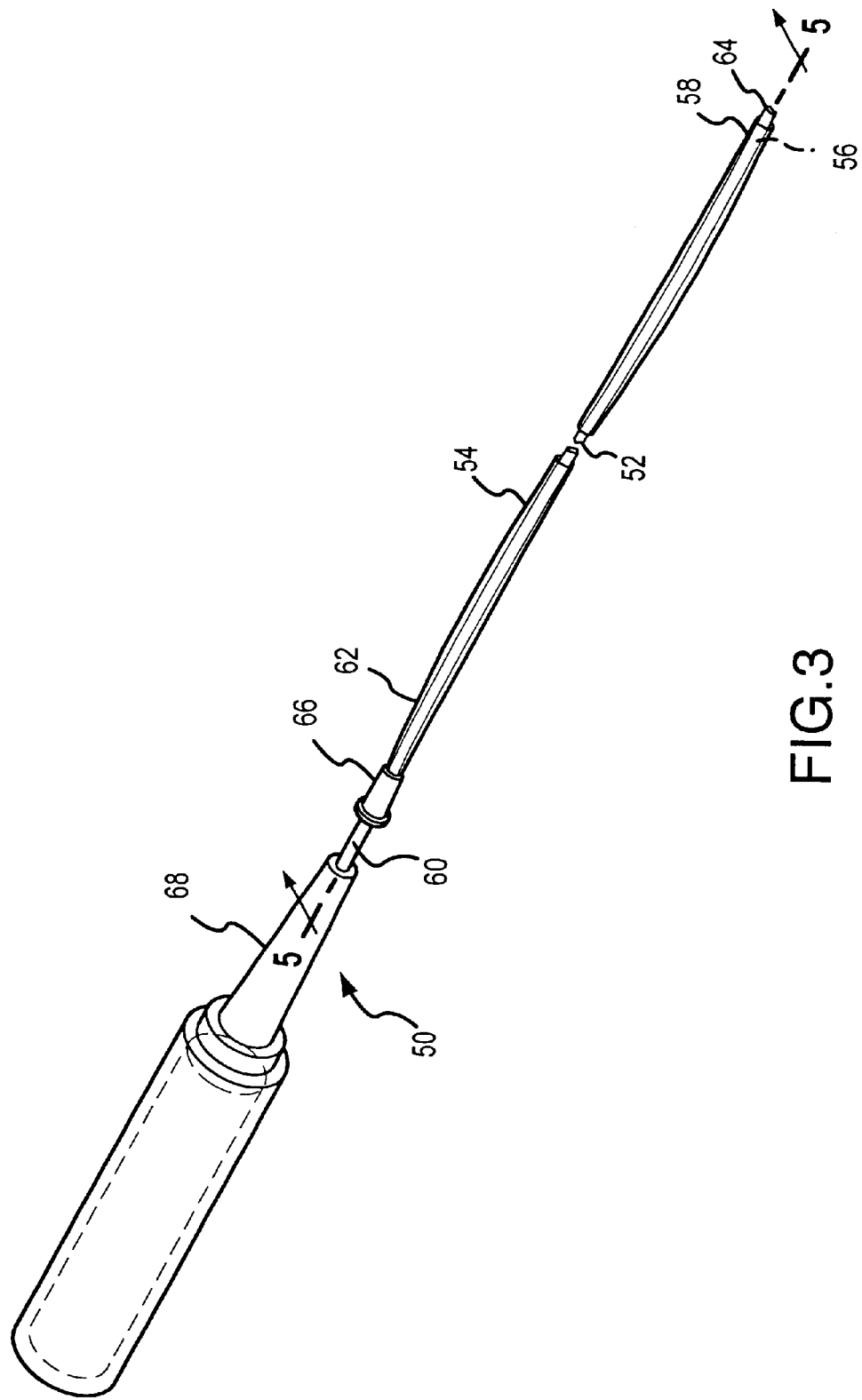
FIG. 3 is an isometric view of a thin-walled, elastic sheath formed in accordance with one embodiment of the present invention placed in a relaxed state over an insertion tube of a flexible endoscope.
Figure 4:
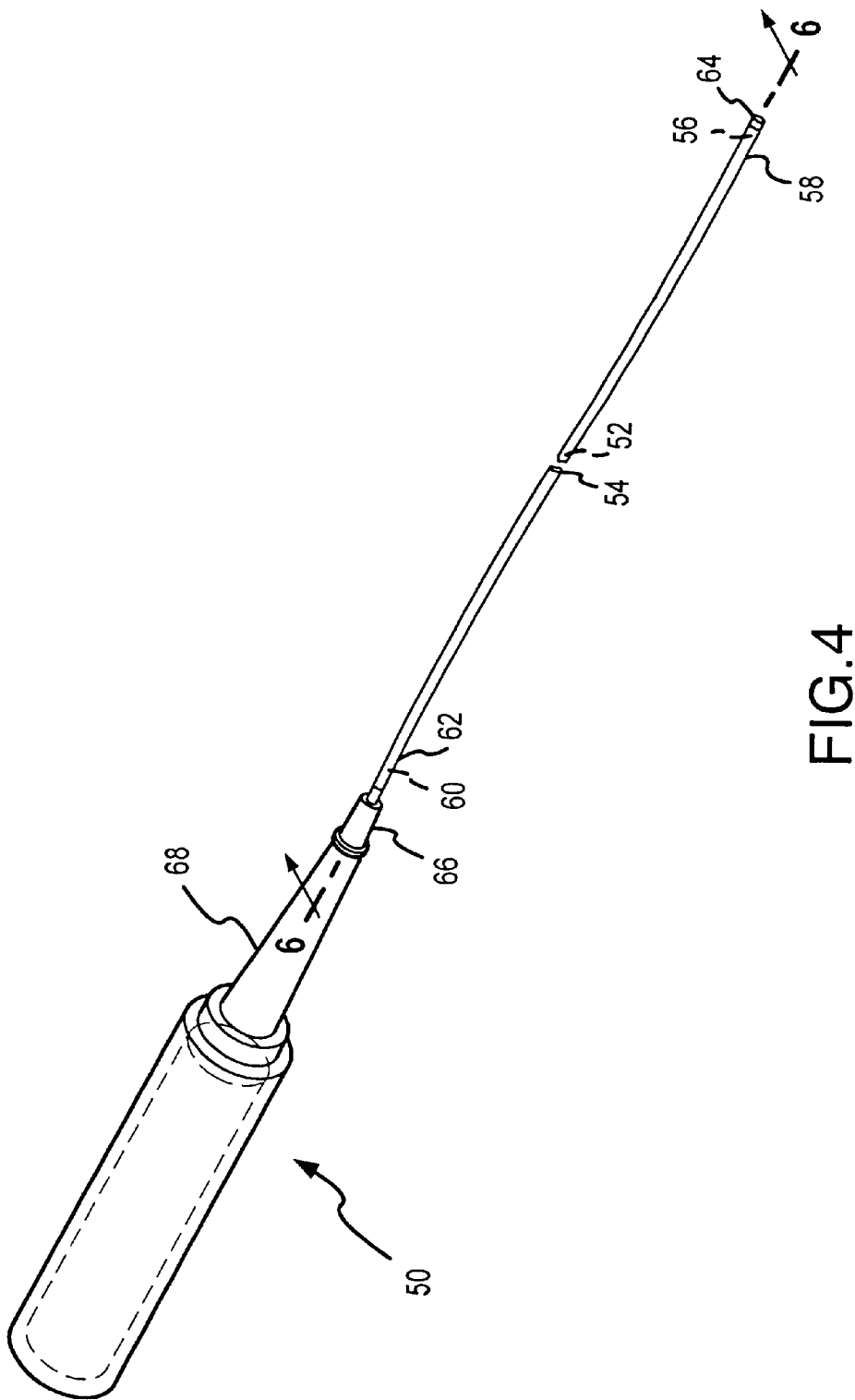
FIG. 4 is an isometric view of the sheath of FIG. 3 in an installed position stretched axially over the insertion tube of the flexible endoscope.
Figure 5:
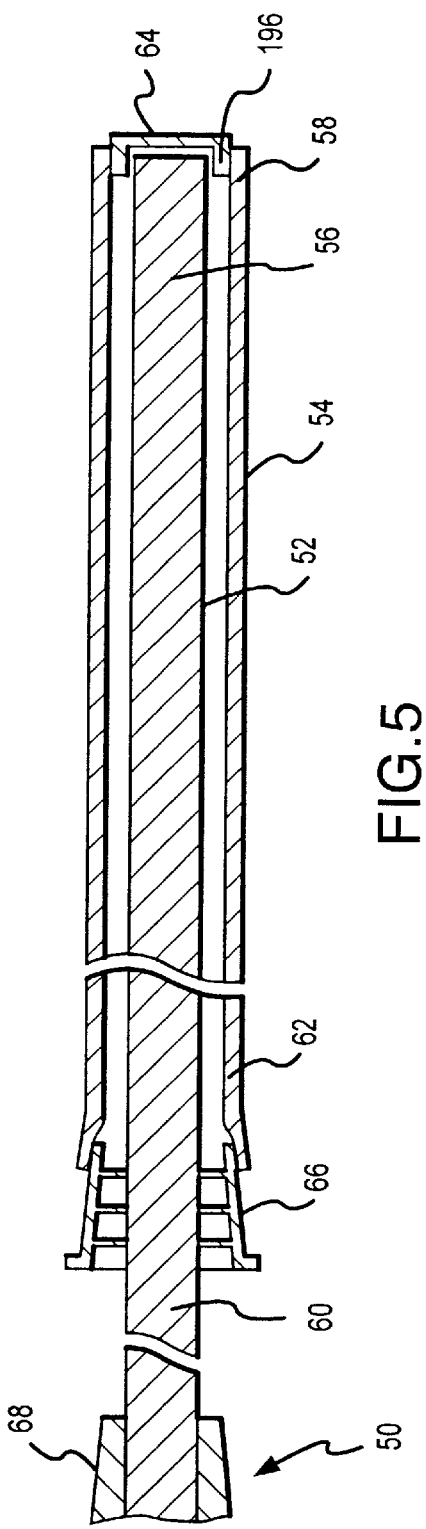
FIG. 5 is a partial cross-sectional view of the sheath and endoscope of FIG. 3 as viewed along Section 5—5.

FIGS. 3–6 illustrate a medical device, for example an endoscope 50 having an insertion tube 52, and a non-extruded, thin-walled, elastic sheath 54 formed in accordance with an embodiment of the invention. As best seen in FIGS. 3 and 5, the elastic sheath 54 is shaped and sized so its diameter is slightly larger than the insertion tube's diameter. The insertion tube 52 can be easily inserted into the elastic sheath 54 until a distal end 56 of the insertion tube 52 just contacts a distal end 58 of the elastic sheath 54. The elastic sheath 54 in FIG. 3 is thus in its relaxed state, having a relaxed outside diameter, a relaxed inner diameter, and a relaxed wall thickness. The elastic sheath 54 has a relaxed wall thickness in the range of up to and including approximately 0.009 inches, and preferably in the range of approximately 0.002 to 0.009 inches, inclusive, and more preferably in the range of approximately 0.002 to 0.006 inches, inclusive.

Figure 6:
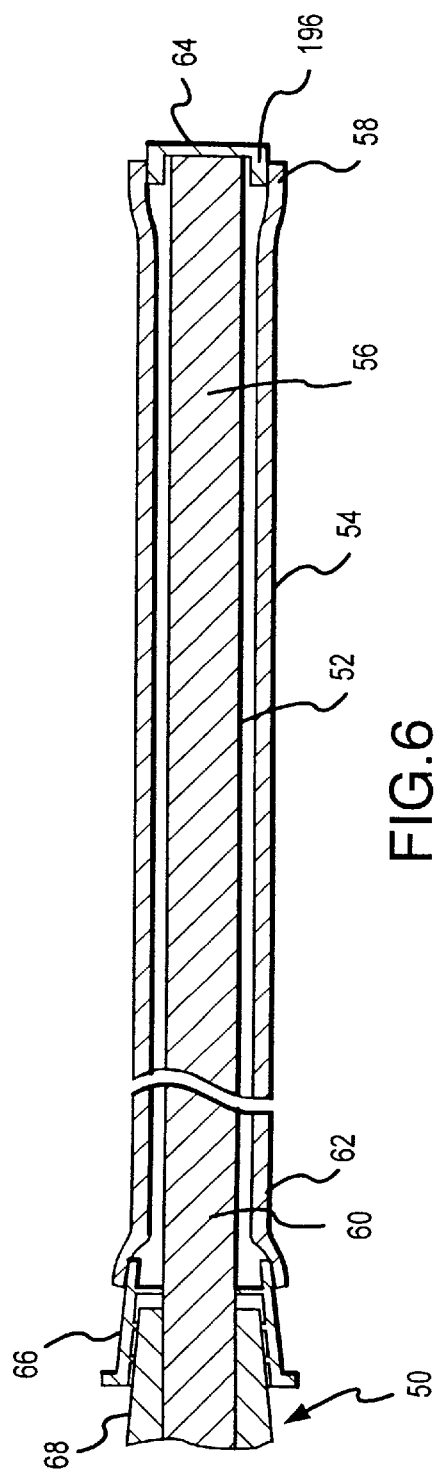
FIG. 6 is a partial cross-sectional view of the sheath and endoscope of FIG. 4 as viewed along Section 6—6.

FIGS. 4 and 6 illustrate the elastic sheath 54 stretched axially over the insertion tube 52 until a proximal end 62 of the elastic sheath 54 aligns with a proximal end 60 of the insertion tube 52. The elastic sheath 54 is thus in a stretched, installed position, having a stretched outside diameter, a stretched inner diameter, and a stretched wall thickness. The stretched inner diameter, stretched outer diameter, and stretched wall thickness illustrated in FIG. 6 are smaller than the similar dimensions relaxed in FIG. 5. When the elastic sheath 54 is in the installed position over the insertion tube 52, the elastic sheath and endoscope are ready for use in an endoscopic procedure while the insertion tube remains isolated from a contaminated environment.

As best seen in FIGS. 5 and 6, the extreme distal end 58 of the elastic sheath 54 is sealably connected to an end cap 64. The end cap 64 can be integral with the elastic sheath 54, or can be formed separately from the sheath and sealably attached thereto. In the latter case, the end cap 64 can be formed from a different material than the elastic sheath 54, such as an inelastic polymer, in order to provide selected optical characteristics that may be different than those of the elastomeric material. For example, the end cap 64 can be formed from a clear, inelastic polymer to provide better visibility for use with an insertion tube 52 having a viewing window at its distal end 56.

The proximal end 62 of the elastic sheath 54 terminates in a fitting, such as a collar 66. Similar to the end cap 64, the collar 66 can be integral with the sheath 54 or separate from and bonded to the elastic sheath 54. As best illustrated in FIG. 6, the collar 66 is sized and shaped to resiliently engage a headpiece 68 of the endoscope 50 to retain the sheath 54 on the insertion tube 52 during a procedure.

Figure 7:
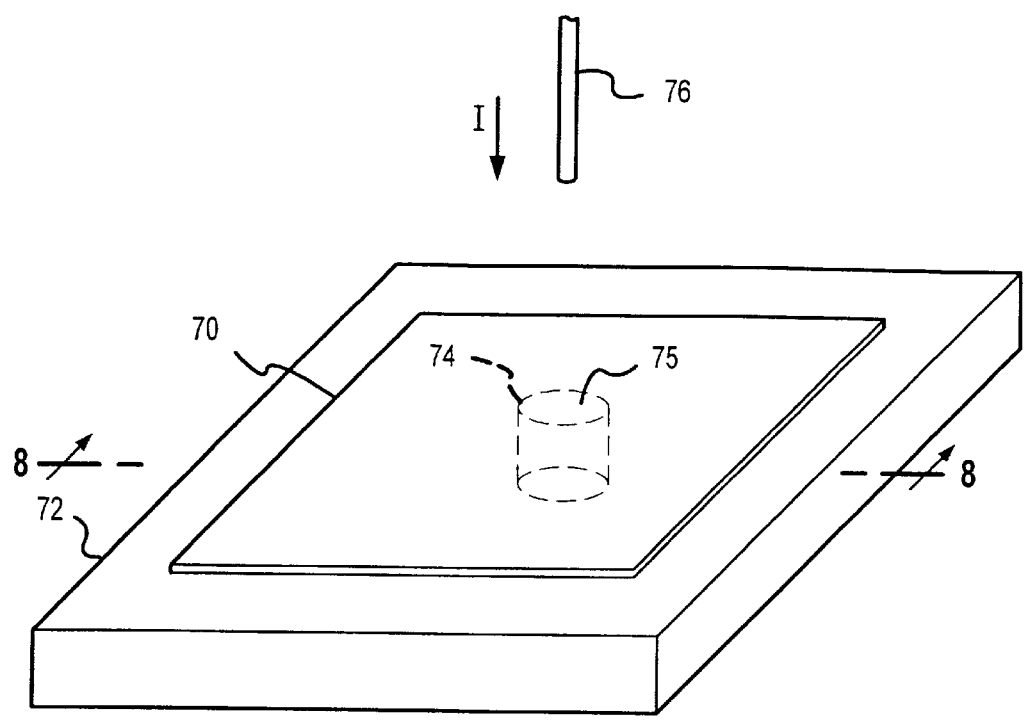
FIG. 7 is an isometric view of a sheet of partially-heated, elastomeric material and a support structure below a forming tool according an embodiment of the method of the present invention before the sheath has been formed.
Figure 8:
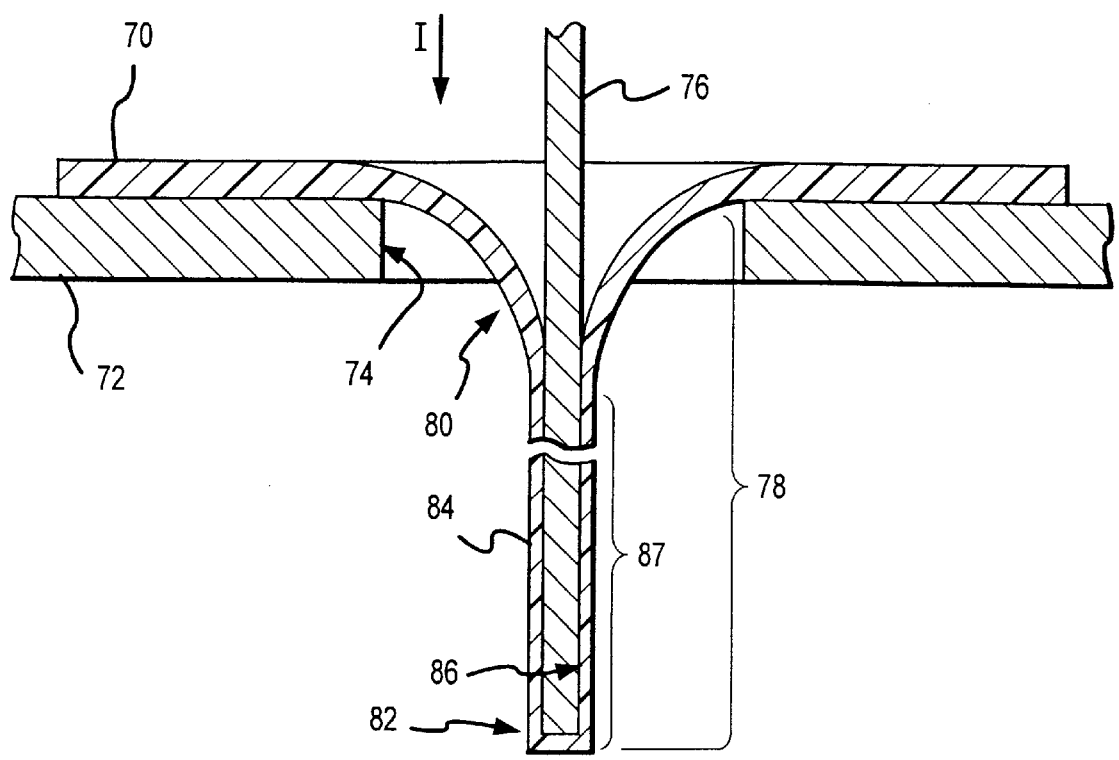
FIG. 8 is an enlarged cross-sectional view of FIG. 7 viewed along Section 8—8 after the sheath has been formed.

FIGS. 7 and 8 illustrate a method of manufacturing the thin-walled, elastic sheath 54. The method uses a sheet 70 of elastomeric material, such as a polyurethane, that contains friction-reducing additives or slip agents, such as wax, oil, silicon or silica. In the illustrated embodiment, the sheet 70 has an initial thickness of about 0.042 inches, although the thickness of the sheet 70 can vary based on the desired length and thickness of the sheath 54 being formed. The sheet 70 of the elastomeric material is retained on a substantially flat support 72 having a central opening 74 extending therethrough. A portion of the elastomeric sheet 70 above the central opening is heated by a conventional heating device to a selected malleable temperature to form a malleable, heated portion 75 of the sheet 70. A forming tool 76 is then pressed into the heated portion 75 in a direction substantially normal to the plane of the sheet 70, illustrated by the direction I. In the illustrated embodiment, the forming tool 76 has a generally circular cross-section. The forming tool 76, however, could also have an oval, polygonal or other suitable cross-sectional shape. As the forming tool 76 is pressed into the heated portion 75, the elastomeric sheet 70 stretches beyond its modulus of elasticity to form an elongated, thin-walled protrusion 78 (FIG. 8). The protrusion 78 will eventually become all or a portion of the sheath 54, as the excess material from the elastomeric sheet 70 is trimmed from the protrusion 78.

As illustrated in FIG. 8, the protrusion 78 has an open proximal portion 80, a closed distal portion 82 spaced away from the open proximal portion 80, and sidewalls 84 extending between the proximal and distal portions. The closed distal portion 82 and the sidewalls 84 define an interior 86 of the protrusion 78. As the forming tool 76 is moved in the direction I, the interior 86 of a conforming portion 87 at the distal portion 82 of the protrusion 78 begins to closely conform to the outer shape of the forming tool. As the forming tool 76 is moved further in the direction I, the conforming portion 87 of the protrusion 78 progressively conforms to more of the length of the forming tool 75. The forming tool 76 is moved in the direction I until the length of the conforming portion 87 of the protrusion 78 is at least as long as the desired length of the elastic sheath 54 being formed. The elastic sheath 54 can be as long as the insertion tube 52 for which it will be used, or it can be shorter than the insertion tube 52 (FIG. 5) to allow the elastic sheath 54 to be stretched axially over the insertion tube when installed. The forming tool 76 can be stopped when the conforming portion 87 is at the desired length, or it can be moved further if desired to reduce the thickness of the sidewalls 84. The thickness of the sidewalls 84 in one embodiment is in the range of approximately 0.002 to 0.009 inches, inclusive, and preferably in the range of approximately 0.002 to 0.006 inches, inclusive, or can be thinner than 0.002 inches. After the elongated, thin-walled conforming portion 87 of the protrusion 78 is formed to a desired length and thickness, the protrusion is allowed to cool to a temperature at which the elastomeric material is no longer malleable.

After the protrusion 78 has cooled, the forming tool 76 is removed from the protrusion 78 and the protrusion is cut to separate the elastic sheath 54 from the elastomeric sheet 70. The distal portion 82 of the protrusion 78 can be left on what is now the elastic sheath 54, or it can be removed and replaced with an end cap 64 (FIG. 6). If needed during manufacturing, the sheath 54 can then be trimmed at the distal end to the desired length before attaching the end cap.

The elastomeric material used with the above embodiment of the present invention is a thermoplastic, elastomeric material, such as polyurethane containing one or more conventional slip agents, such as wax, oil, silicone or silica. Such slip agents are commonly used in the field of elastomeric materials, and an individual having ordinary skill in such an art will understand how to treat the elastomeric material to provide the desired properties for reduced friction. The treated elastomeric material allows for small diameter, thin-walled elastic medical components that can be easily, inexpensively, and quickly manufactured.

Embodiments of the present invention have a number of advantages over the sheaths of the prior art and the methods of making such sheaths. Because the elastomeric material is allowed to cool on the forming tool, the forming tool prevents the sheath from collapsing and sticking to itself while the elastomeric material is heated and tacky. This is an improvement over traditional extruded sheaths that could collapse during forming. If the sheath collapsed while the elastomeric material was hot and tacky, the sheath could be ruined.

Also, because the elastic sheath 54 is made from an elastomeric material treated with slip agents, the sheath can be formed with a relaxed inner diameter only slightly larger than an outside diameter of the insertion tube 52 and still be easily installed. The slip agents allow the insertion tube to be easily inserted into the elastic sheath 54 without the distal end 56 of the insertion tube 52 binding, catching, or excessively distorting the elastic sheath 54 during installation. Thus the need for baggy sheaths can be eliminated. The need for additional equipment and features previously used to radially expand the tight-fitting, elastic sheath during installation are also eliminated.

Further, because the elastic sheath 54 is made from an elastomeric material, the diameter and wall thickness of the elastic sheath 54 decrease as the sheath is stretched axially over the insertion tube. Accordingly, the overall cross-section of the sheathed insertion tube may be minimized, thereby reducing the pain or discomfort experienced by a patient. Stretching the sheath also creates an axial restoring force in the elastomeric material which retains the end cap 64 at the distal end 58 of the elastic sheath 54 in contact and alignment with the distal end 56 of the insertion tube 52.

While the elastic sheath 54 and the method of making the sheath are discussed herein with reference to an endoscope 50, the method of the present invention is equally applicable to other medical components. For example, the medical component in alternate embodiments can be a catheter, optical imaging medical equipment, and non-optical imaging medical equipment.

Figure 9:
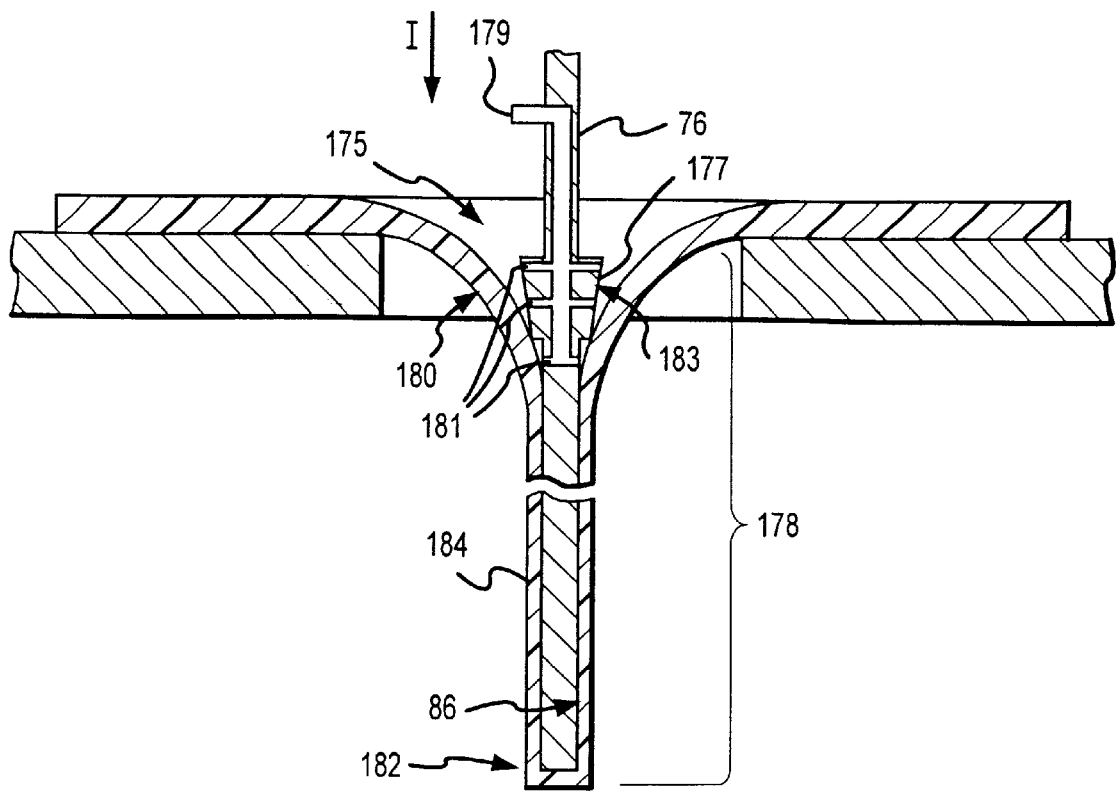
FIG. 9 is a cross-sectional view of another forming tool, a sheet of elastomeric material and a support structure according to another embodiment of the present invention after the sheath has been partially formed.
Figure 10:
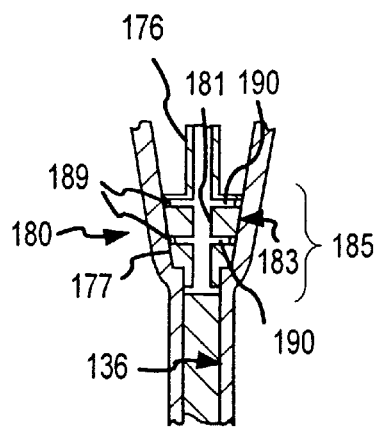
FIG. 10 is a partial, cross-sectional view of a proximal portion of the sheath of FIG. 9 after the sheath has been fully formed.

FIGS. 9 and 10 illustrate an alternate embodiment of the method of the present invention. In this particular embodiment, best illustrated in FIG. 9, the forming tool 176 has a tapered annular portion 177 at a point selected to correspond to a proximal end 180 of the elastic sheath 178. The annular portion 177 is provided in this embodiment in order to form an integral collar 185 (FIG. 10) at the sheath's proximal end 180. After the forming tool 176 is moved to a point at which the elastomeric sheet's malleable heated portion 175 has at least partially conformed to the annular portion 177, a radially inward force is applied to the sidewalls 184 to force the sidewalls against the annular portion 177. In the illustrated embodiment, the radially inward force is applied to the sidewalls 184 by a vacuum source (not shown) attached to a vacuum port 179 in the forming tool 176. A partial vacuum is applied to the interior 186 of the sheath 178 via a number of ports 181 in the forming tool 176. In an alternate embodiment, a radially inward force is applied by pressing on the exterior of the sheath's sidewalls. As illustrated in FIG. 10, the forming tool's annular portion 177 has a plurality of passages 190 into which a portion of the sidewalls 184 is drawn when the radially inward force is applied. The passages 190 are shaped and sized to form retention members 189 in the proximal end 180 of the sheath 178 that releasably engage the distal end of the endoscope control body (not shown). In one embodiment, the passages 190 are shaped into annular grooves extending about the annular portion 177. In that embodiment, the retention members 189 are formed into annular inward projections. Thus, the elastic sheath 178 is formed with an integral proximal fitting used for retaining the sheath on the endoscope in the installed position. In the illustrated embodiment, the retention members 189 are annular in shape and have rectilinear cross-sections. The retention members 189, however, can have other shapes and sizes.

As described above, the cooled, elastic sheath 178 is then removed from the forming tool 176 and the elastic sheath 178 is trimmed or cut near the proximal end 180 to remove excess material from the sheath 178. In the exemplary embodiment, the sheath's distal end 182 may also be trimmed, and an end cap, such as that illustrated in FIGS. 5 and 6, is adhered or otherwise connected to the distal end 182. In one embodiment, the sheath's distal end 182 extends over the outside of the endcap and is sealably bonded in place. In an alternate embodiment, the sheath's distal end 182 is sealably bonded to the inside of the endcap. The sheath 178 is then ready for use with an endoscope to perform a selected endoscopic procedure without contaminating the endoscope's insertion tube.

From the foregoing it will be appreciated that, although specific embodiments of the invention have been described herein for purposes of illustration, various modifications may be made without deviating from the spirit and scope of the invention. Also, although the various embodiments of the invention have been described as being used to form complex components, it will be understood that relatively simple components may also be formed in accordance with the invention. Accordingly, the invention is not limited except as by the appended claims.

What is claimed is:

1. A method of forming a thin-walled, elastic sheath for an endoscopic insertion tube, the insertion tube having a length and a diameter, the method comprising:

heating a portion of a sheet of an elastomeric material to form a malleable heated portion of the sheet;

pressing an elongated forming tool into the heated portion of the sheet;

stretching the heated portion with the forming tool until an elastic conforming portion of the sheet is conformed to a selected portion of the forming tool; and removing the forming tool from the elastic conforming portion of the sheet to leave the elastic sheath.

2. The method of claim 1 further comprising, prior to removing the forming tool, cooling the heated portion of the sheet until the elastic conforming portion of the sheet is no longer malleable.

3. The method of claim 1 wherein the forming tool is sized and shaped such that stretching the heated portion results in the elastic sheath in the relaxed shape having a diameter in the range of approximately 0.140 inches and 0.190 inches, inclusive.

4. The method of claim 1 wherein stretching the heated portion with the forming tool comprises moving the forming tool until the elastic conforming portion of the sheet in the relaxed state has a thickness approximately equal to or less than 0.006 inches.

5. The method of claim 4 wherein the outside diameter of the forming tool measures between 0.140 inches and 0.190 inches, inclusive, and wherein stretching the heated portion with the forming tool comprises moving the forming tool until the internal diameter of the elastic conforming portion of the sheet is closely conformed to a diameter of the forming tool.

6. The method of claim 1 wherein stretching the heated portion with the forming tool comprises stretching the heated portion until the elastic conforming portion of the sheet in the relaxed state has a thickness of approximately 0.003 inches.

7. The method of claim 1, further comprising forming an aperture at the distal end of the elastic conforming portion of the sheet and sealably attaching an end cap to the distal end.

8. The method of claim 7 wherein the end cap has an outer surface, and sealably attaching the end cap comprises inserting the end cap into the aperture and bonding the distal end of the elastic conforming portion to the outer surface of the end cap.

9. The method of claim 7 wherein the forming tool has a fitting portion positioned to align with a proximal end of the elastic conforming portion of the sheet when the elastic conforming portion of the sheet is fully stretched over the forming tool, and further comprising exerting an inwardly directed force on the proximal end of the elastic conforming portion of the sheet while the heated portion is malleable, the force being sufficient to conform the proximal end of the elastic conforming portion of the sheet to the fitting portion.

10. The method of claim 9 wherein the conforming portion has an interior and an exterior, and wherein exerting the inwardly directed force includes creating an interior pressure in the interior of the conforming portion less than an exterior pressure that is exterior of the conforming portion causing the proximal portion of the elastic conforming portion of the sheet to conform to the fitting portion.

11. The method of claim 9 wherein the conforming portion has an interior, and wherein exerting the inwardly directed force includes creating a partial vacuum in the interior when the heated portion is malleable to draw the proximal portion of the elastic conforming portion of the sheet into close conformity with the fitting portion.

12. The method of claim 1, further comprising, prior to heating a portion of the sheet to form the malleable heated portion of the sheet, forming a sheet of an elastomeric material including a slip agent.

13. The method of claim 12 wherein the slip agent comprises silicone.

14. A method of forming an elastic sheath for an insertion tube on a medical component, the insertion tube having a length and a diameter, the method comprising:
    forming a malleable portion of a sheet of an elastomeric material;
    pressing an elongated forming tool into the malleable portion of the sheet until an elastic conforming portion of the sheet is conformed to a selected portion of the forming tool; and
    removing the forming tool from the elastic conforming portion of the sheet to leave the elastic sheath.

15. The method of claim 14 wherein forming a malleable portion of a sheet of an elastomeric material comprises heating a portion of a sheet of an elastomeric material.

16. The method of claim 14, further comprising, prior to removing the forming tool, cooling the heated portion of the sheet until the elastic conforming portion of the sheet is no longer malleable.

17. The method of claim 14 wherein the forming tool is sized and shaped such that pressing a forming tool into the malleable portion results in the elastic sheath in the relaxed shape having a diameter in the range of approximately 0.140 inches and 0.190 inches, inclusive.

18. The method of claim 14 wherein pressing a forming tool into the malleable portion comprises moving the forming tool until the elastic conforming portion of the sheet in the relaxed state has a thickness approximately equal to or less than 0.006 inches.

19. The method of claim 18 wherein the outside diameter of the forming tool measures between 0.140 inches and 0.190 inches, inclusive, and wherein pressing a forming tool into the malleable portion comprises moving the forming tool until a diameter of the elastic conforming portion of the sheet is closely conformed to the outside diameter of the forming tool.

20. The method of claim 14 wherein pressing a forming tool into the malleable portion comprises moving the forming tool until the elastic conforming portion of the sheet in the relaxed state has a thickness of approximately 0.003 inches.

21. The method of claim 14, further comprising forming an aperture at the distal end of the elastic conforming portion of the sheet and sealably attaching an end cap to the distal end.

22. The method of claim 21 wherein the end cap has an outer surface, and sealably attaching the end cap comprises inserting the end cap into the aperture and bonding the distal end of the elastic conforming portion to the outer surface of the end cap.

23. The method of claim 14 wherein the forming tool has a fitting portion positioned to align with a proximal end of the elastic conforming portion of the sheet when the elastic conforming portion of the sheet is fully stretched over the forming tool, and further comprising exerting an inwardly directed force on the proximal end of the elastic conforming portion of the sheet, the inwardly directed force being sufficient to conform the proximal end of the elastic conforming portion of the sheet to the fitting portion.

24. The method of claim 23 wherein the conforming portion has an interior and an exterior, and wherein exerting the inwardly directed force includes creating an interior pressure in the interior of the conforming portion less than an exterior pressure that is exterior of the conforming portion causing the proximal portion of the elastic conforming portion of the sheet to conform to the fitting portion.

25. The method of claim 23 wherein the conforming portion has an interior, and wherein exerting the inwardly directed force includes creating a partial vacuum in the interior to draw the proximal portion of the elastic conforming portion of the sheet into close conformity with the fitting portion.

26. The method of claim 14 further comprising, prior to heating a portion of the sheet to form the malleable heated portion of the sheet, forming a sheet of an elastomeric material including a slip agent.

27. The method of claim 26 wherein the slip agent comprises silicone.

28. An elastic sheath installed on an endoscopic insertion tube made by a process comprising:
    heating a portion of a sheet of an elastomeric material to form a malleable heated portion of the sheet;
    pressing an elongated forming tool into the heated portion of the sheet;
    stretching the heated portion with the forming tool until an elastic conforming portion of the sheet is conformed to a selected portion of the forming tool and has a length in a relaxed state that is shorter than a length of the insertion tube; and
    removing the forming tool from the elastic conforming portion of the sheet to leave the elastic sheath.

29. The elastic sheath of claim 28 wherein the elastomeric material forming the sheath further comprises a slip agent.

30. The elastic sheath of claim 29 wherein the slip agent comprises silicone.

31. The elastic sheath of claim 28 wherein the process further comprises forming an aperture at a distal end of the elastic conforming portion of the sheet.

32. The elastic sheath of claim 28 the process further comprises attaching an end cap at a distal end of the elastic conforming portion of the sheet.

33. The elastic sheath of claim 32 wherein attaching an end cap at a distal end of the elastic conforming portion of the sheet comprises integrally forming an end cap at a distal end of the elastic conforming portion of the sheet.

34. The elastic sheath of claim 32 wherein the end cap has an outer surface, and wherein attaching the end cap comprises inserting the end cap into an aperture and bonding the distal end of the elastic conforming portion to the outer surface of the end cap.

35. The elastic sheath of claim 32 wherein the end cap includes a window that is at least partially transparent to light.

36. An elastic sheath assembly installed on an endoscope having an elongated insertion tube projecting from an engagement portion, the sheath assembly comprising:

an elongated, elastic tubular portion sized to receive and extend around a perimeter of the insertion tube when the insertion tube is inserted into the sheath assembly;

a proximal fitting attached to the tubular portion and having an open end adapted to fittingly receive at least part of the engagement portion when the insertion tube is inserted into the tubular portion; and a closed distal end attached to the elastic tubular portion at an end opposite from the proximal fitting;

and wherein the tubular portion is formed by a process comprising:

heating at least a portion of a sheet of an elastomeric material to form a malleable heated portion of the sheet;

pressing an elongated forming tool into the heated portion of the sheet;

stretching the heated portion with the forming tool until an elastic conforming portion of the sheet is conformed to a selected portion of the forming tool; and removing the forming tool from the elastic conforming portion of the sheet to leave the elastic sheath, and wherein the tubular portion is adapted to be stretchable axially over the insertion tube to retain the closed distal end of the sheath against a distal end of the insertion tube when at least a part of the engagement portion is fittingly received into at least a portion of the proximal fitting, an inner diameter of the tubular portion being sized such that the tubular portion is not stretched radially outward by the insertion tube when at least a part of the engagement portion is fittingly received into at least a portion of the proximal fitting and the insertion tube is approximately straight.

37. The elastic sheath assembly of claim 36 wherein heating at least a portion of a sheet of an elastomeric material comprises heating at least a portion of a polyurethane sheet.

38. The elastic sheath assembly of claim 36 wherein heating a portion of a sheet of an elastomeric material comprises heating a portion of a sheet of an elastomeric material including a slip agent.

39. The elastic sheath assembly of claim 36 wherein the closed distal end is integrally formed with the elastic tubular portion.

40. The elastic sheath assembly of claim 36 wherein the proximal fitting is integrally formed with the elastic tubular portion.

41. An elastic sheath assembly installed on an endoscope having an elongated insertion tube projecting from an engagement portion, the sheath assembly comprising:

an elongated, elastic tubular portion adapted to extend around a perimeter of the insertion tube when the insertion tube is inserted into the sheath assembly, and a closed distal end attached to the elastic tubular portion, the elastic tubular portion being formed by a process comprising:

heating at least a portion of a sheet of an elastomeric material to form a malleable heated portion of the sheet;

pressing an elongated forming tool into the heated portion of the sheet;

stretching the heated portion with the forming tool until an elastic conforming portion of the sheet is conformed to a selected portion of the forming tool; and removing the forming tool from the elastic conforming portion of the sheet to leave the elastic sheath, and wherein the tubular portion is adapted to be stretchable axially over the insertion tube to retain a closed distal end of the tubular portion against a distal end of the insertion tube when at least a part of the engagement portion is fittingly received into at least a portion of the proximal fitting, an inner diameter of the tubular portion being sized such that the tubular portion is not stretched radially outward by the insertion tube when at least a part of the engagement portion is fittingly received into at least a portion of the proximal fitting and the insertion tube is approximately straight.

42. The elastic sheath assembly of claim 41, further comprising a proximal fitting attached to the tubular portion and having an open end adapted to fittingly receive at least part of the engagement portion when the insertion tube is inserted into the tubular portion.

43. The elastic sheath assembly of claim 41 wherein heating at least a portion of a sheet of an elastomeric material comprises heating at least a portion of a sheet of an elastomeric material that includes a slip agent.

44. The elastic sheath assembly of claim 43 wherein the slip agent comprises an oil.

45. A method of forming a thin-walled, elastic sheath for an endoscopic insertion tube, the method comprising:

providing an elastomeric material;

adding a slip agent to the elastomeric material;

forming the elastomeric material into a sheet;

forming a malleable portion of the sheet;

pressing an elongated forming tool into the malleable portion of the sheet;

stretching the malleable portion with the forming tool until an elastic conforming portion of the sheet is conformed to a selected portion of the forming tool; and removing the forming tool from the elastic conforming portion of the sheet to leave the elastic sheath.

46. The method of claim 45 wherein forming a malleable portion of the sheet comprises heating a portion of the sheet.

47. The method of claim 45, further comprising, prior to removing the forming tool, treating the elastic conforming portion of the sheet until it is no longer malleable.

* * * * *